(12) United States Patent
Remes et al.

(10) Patent No.: US 11,806,166 B2
(45) Date of Patent: Nov. 7, 2023

(54) ELECTRODE APPARATUS AND MEASUREMENT METHOD THEREOF

(71) Applicant: Bittium Biosignals Oy, Kuopio (FI)

(72) Inventors: Arto Remes, Kuopio (FI); Juha Myllykangas, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 724 days.

(21) Appl. No.: 16/797,492

(22) Filed: Feb. 21, 2020

(65) Prior Publication Data

US 2021/0259635 A1  Aug. 26, 2021

(51) Int. Cl.
| | | |
|---|---|---|
| A61B 5/251 | (2021.01) | |
| A61B 5/25 | (2021.01) | |
| A61B 5/00 | (2006.01) | |
| A61B 5/369 | (2021.01) | |
| A61B 5/318 | (2021.01) | |

(52) U.S. Cl.
CPC .......... *A61B 5/6839* (2013.01); *A61B 5/251* (2021.01); *A61B 5/318* (2021.01); *A61B 5/369* (2021.01)

(58) Field of Classification Search
CPC ....... A61B 5/6839; A61B 5/369; A61B 5/251; A61B 5/318; A61B 5/254; A61B 5/25; A61B 5/291
See application file for complete search history.

(56) References Cited

U.S. PATENT DOCUMENTS

| | | | | |
|---|---|---|---|---|
| 6,175,753 B1 * | 1/2001 | Menkes | ............... | A61B 5/6814 600/386 |
| 6,201,982 B1 * | 3/2001 | Menkes | ................ | A61B 5/411 600/386 |
| 2012/0136233 A1 * | 5/2012 | Yamashita | ........... | A61B 5/6803 600/393 |

FOREIGN PATENT DOCUMENTS

| | | |
|---|---|---|
| JP | 2006-006667 | 1/2006 |
| JP | 2006006667 A * | 1/2006 |

(Continued)

OTHER PUBLICATIONS

Kumada, Yoshiyuki, Translation of JP 2006006667A, Jan. 12, 2006, Olympus Corp (Year: 2006).*

(Continued)

*Primary Examiner* — Adam Z Minchella
(74) *Attorney, Agent, or Firm* — Nixon & Vanderhye PC (57) ABSTRACT

An electrode apparatus is applicable on a skin with hair of a mammal for measuring an electrical bio-signal. The electrode apparatus comprises cylindrical chambers, each of which comprises a wall, which forms a cavity within the cylindrical chambers, a roof at a first end of each of said cylindrical chambers, a second end of said cylindrical chambers opposite to the first end being open, and at least one electrode. An elongated structure is located within each of the cylindrical chambers, and comprises a first portion parallel to a central axis of a cylindrical chamber within which it is. A first end of the elongated structure, the first end of the elongated structure belonging to the first portion, is attached to the roof. At least one second portion, each comprising a second end opposite to the first end, deviates from a direction of the central axis of a cylindrical chamber within which it is. The elongated structure rotatable in order to bundle hair when applied to the mammal so as to improve a contact of the electrode with the skin of the mammal.

20 Claims, 5 Drawing Sheets

(56) References Cited

FOREIGN PATENT DOCUMENTS

WO 01/01856 1/2001
WO 01/01857 1/2001

OTHER PUBLICATIONS

Kumada Y, Translation of JP-2006006667-A, Jan. 2006 (Year: 2006).*
Search Report dated Jun. 10, 2021 in corresponding European Application No. 21156207, 2 pages.

* cited by examiner

ELECTRODE APPARATUS AND MEASUREMENT METHOD THEREOF

FIELD

The invention relates to an electrode apparatus and a measurement method thereof.

BACKGROUND

When an EEG (Electroencephalography) measurement is performed, an electrode cap is typically put on a patient's head. Because the head is typically hairy, the hair causes problems to an electrical contact between the electrodes of the cap and the skin of the patient. Typically patient's hair is removed or moved out of the way of each different electrode position manually. This procedure takes a lot of time and yields an uneven outcome that often needs more and more adjusting.

Additionally, there is a problem with different head sizes and a relatively short period of time before conventional EEG electrodes dry out when applied to the head. Dry electrodes typically increase the impedance drastically and induce noise and artefacts to the measurement. Furthermore, it is at least somewhat complicated to place the EEG electrodes on correct positions on the head. Similar challenging problems may also relate to the ECG (electrocardiography) measurements. As a conclusion, an extensive EEG or ECG measurement is currently time consuming and difficult to prepare. Hence, there is a need to improve the measurement.

BRIEF DESCRIPTION

The present invention seeks to provide an improvement in the measurements.

The invention is defined by the independent claims. Embodiments are defined in the dependent claims.

LIST OF DRAWINGS

Example embodiments of the present invention are described below, by way of example only, with reference to the accompanying drawings, in which.

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1:
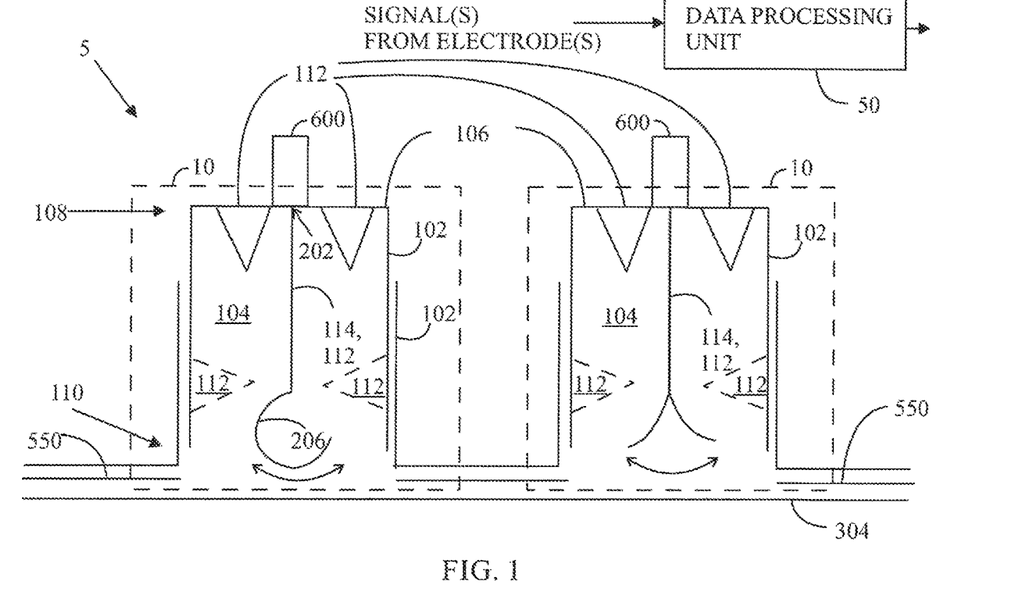
FIG. 1 illustrates an example of cylindrical chambers.
Figure 7A:
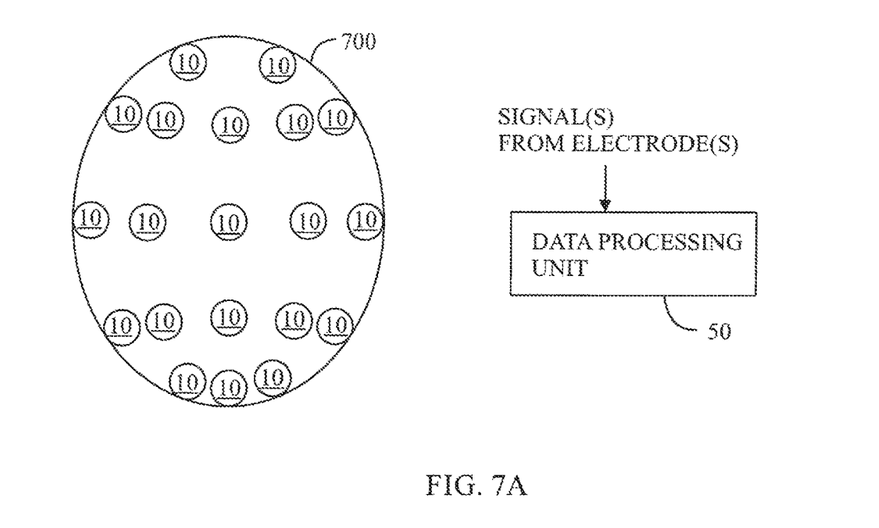
FIGS. 7A and 7B illustrate an example of a cap electrode arrangement.
Figure 7B:
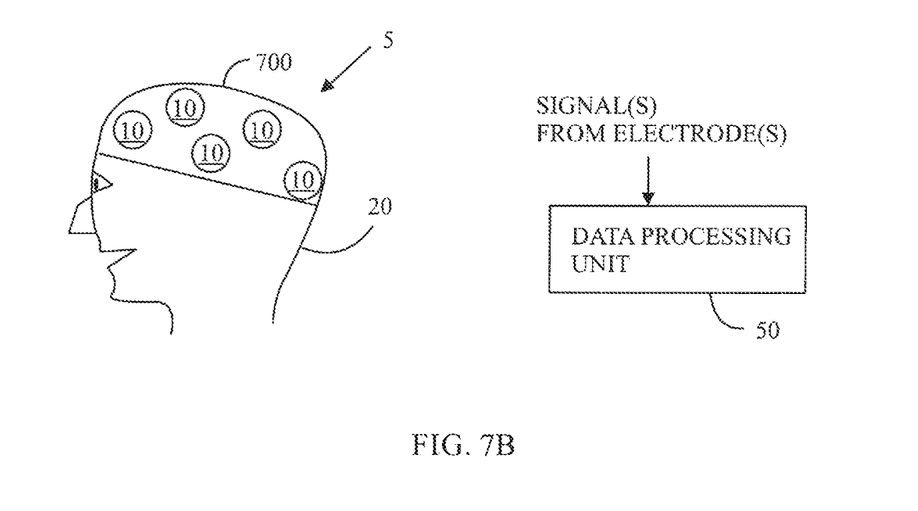

FIG. 1 illustrates an example of an electrode apparatus 5, which can be applied on a skin 304 with hair of a mammal 20 (see FIGS. 7B and 8) for measuring an electrical biosignal. The hair is not shown in FIG. 1. The electrode apparatus 5 comprises one or more cylindrical chambers 10. The cylinder shape of the cylindrical chamber 10 may be a right circular cylinder (shown in Figures) or an oblique circular cylinder (not shown in Figures). The at least one of the cylindrical chambers 10 comprises a wall 102, which forms a cavity 104 within said at least one of the cylindrical chamber 10. A roof 106 locates at a first end 108 of said at least one of the cylindrical chambers 10. A second end 110 of said at least one of the cylindrical chambers 10 opposite to the first end 108 is open. The cylindrical chamber 10 also comprises at least one electrode 112.

One or more of the at least one cylindrical chamber 10 further comprises an elongated structure 114 within said at least one of the cylindrical chambers 10.

Signals from the electrodes 112 in the cylindrical chambers 10 may be fed to a data processing unit 50 for processing and analyzing the signals. The analysis may be parametrical or non-parametrical. The analysis may be performed in a time domain, in a frequency domain, in a time-frequency domain and/or a nonlinear analysis may be performed.

Figure 2:
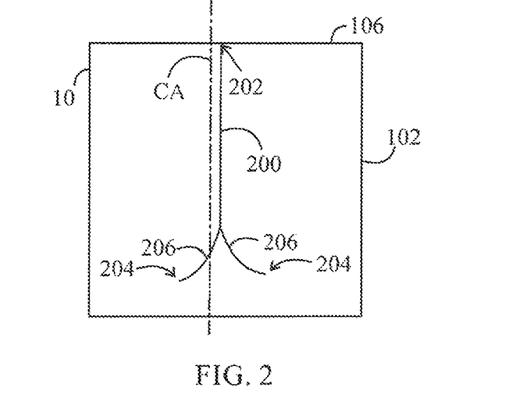
FIG. 2 illustrates an example of a cylindrical chamber.

As shown in FIG. 2, the elongated structure 114 comprises a first portion 200, which is parallel to a central axis CA of the cylindrical chambers 10 within which it locates. The first portion 200 may be fully or partially parallel to the central axis CA. Then the first portion 200 may have a directional vector component that is parallel to the central axis CA. A first end 202 of the elongated structure 200 is attached to the roof 106 of said cylindrical chamber 10, the first end 202 of the elongated structure 10 belonging to the first portion 200. In an embodiment, the first portion 200 may be straight. In an embodiment, the central axis CA may pass through the first portion 200 of the elongated structure 114.

The elongated structure 114 also comprises at least one second portion 206, and each of the at least one second portion 206 has a second end 204. The at least one second end 204 of the elongated structure 114 is opposite to the first end 202 of the elongated structure 114. It may also be considered that the at least one second end 204 of the elongated structure 114 is opposite to the first end 202 of the elongated structure 114 in a direction of the central axis CA of said the cylindrical chambers 10 within which it locates. The at least one second portion 206 deviates from the central axis CA of the cylindrical chamber 10 within which it locates. Thus, a directional vector component of the at least one second portion 206 may deviate from the central axis CA of said cylindrical chambers 10. That the directional vector component deviates from the central axis CA may mean that a directional vector component of the at least one second portion 206 has a vector component perpendicular to the central axis CA.

The elongated structure 114 is rotatable. When the electrode apparatus 5 is applied to the mammal 20, the elongated structure 114 is rotated, which causes the elongated structure 114 to bundle the hair 300 of the mammal 20. The bundling of the hair 300, in turn, improves a contact of the at least one electrode 112 with the skin 304 of the mammal 20.

In an embodiment, a rotation axis of the elongated structure 114 may be coaxial with the central axis CA of cylindrical chamber 10 within which the elongated structure 114 locates.

Figure 3:
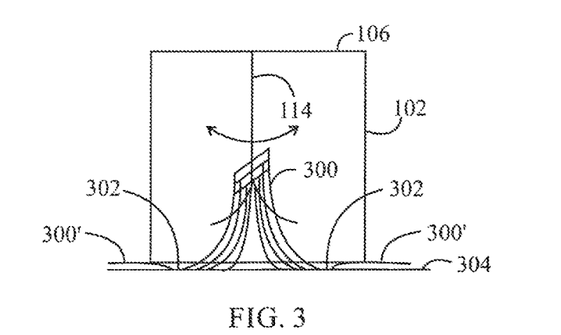
FIG. 3 illustrates an example of a bundle of hair caused by a rotation of an elongated structure within a cylindrical chamber.

FIG. 3 shows an example of how the rotatable elongated structure 114 improves the contact of the at least one electrode 112. The rotation of the elongated structure 114 pulls up the hair 300 in a bundle. The bundle of the hair 300 is formed on and around the second portion 206 of the elongated structure 114. The hair 300' that is not pulled in the bundles remains in its place. A gap 302 is formed between the hair 300 in the bundle and the hair 300' beside it, the gap 302 exposing skin 304 without the hair. The gap 302 may have a shape of a ring around a rotation axis of the elongated structure 114 on the skin 304.

In an embodiment, the elongated structure 114 may be rotatable with respect to the roof 106. Then, the elongated structure 114 is turned without turning the roof 106 with the elongated structure 114. In an embodiment, the roof 106 may be fixed in an immobile manner to wall 102. In this manner, also the wall 102 does not move with the elongated structure 114.

In an embodiment, the elongated structure 114 may be flexible. Here flexible may mean that the elongated structure 114 is bendable and/or twistable. In an embodiment, the elongated structure 114 may made of flexible polymer. In an embodiment, the elongated structure 114 may be made of flexible plastic. In an embodiment, the elongated structure 114 may be made of flexible silicon. In an embodiment, the elongated structure 114 may be made of flexible rubber. When the elongated structure 114 is flexible, it may also be bendable, elastic, resilient, yielding and/or collapsible. A flexible elongated structure 114 allows the hair 300 to be pulled in a bundle in a gentle manner. The flexible elongated structure 114 also allows a gentle twist and release of the hair 300 of the bundle such that the elongated structure may be disentangle and detach from the hair 300 easily. The flexible, elongated structure 114 may be electrically conductive or electrically insulating.

Figure 4A:
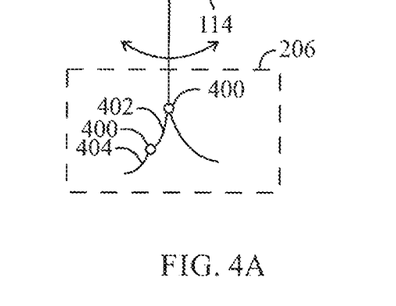
FIGS. 4A to 4C illustrate examples of the elongated structures.

In an embodiment an example of which is illustrated in FIG. 4A, the elongated structure 114, for being flexible, may comprise at least one bendable joint 400, which allows the deviation between the at least one second portion 206 from the central axis. The joint 400 may allow a movement between the first portion 200 and the second portion 206 while the joint 400 is a pivot point. The joint 400 may also allow a movement between sub-portions 402, 404 of one or more of the second portion 206. The elongated structure 114 with the at least one joint 400 may be fully or partly made of metal or polymer.

In an embodiment, the elongated structure 114 may comprise the at least one electrode 112 within the one or more cylindrical chambers 10. That is, the only electrodes or the only electrode 112 of the electrode apparatus 5 may be the elongated structures 114 or the elongated structure 114, respectively. Alternatively, there may be at least one electrode 112 in addition to the at least one elongated structure 114 within the cylindrical chamber 10 where the electrical structure 114 locates. Still alternatively, the elongated structure 114 may not be an electrode at all but an electrical insulator, while there may be at least one electrode 112 the at least one elongated structure 114 within the cylindrical chamber 10 where the elongated structure 114 locates.

In an embodiment, the elongated structure 114 may comprise a shank as a first portion 200, and one or more bends, each of bends being one of said at least one second portion 206.

In an embodiment, the elongated structure 114 has a shape of at least one of the following: a hook, a letter L.

Figure 4B:
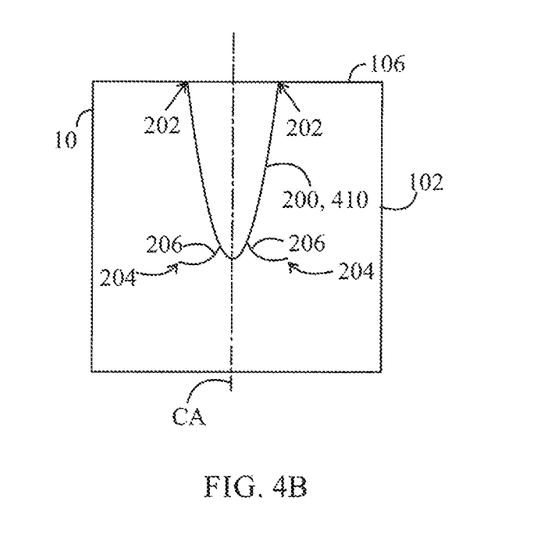

In an embodiment an example of which is illustrated in FIG. 4B, the elongated structure 114 may comprise a loop 410 as the first portion 200. Here the loop refers to a shape of a conic section. That is, the first portion 200 may have an average shape of the conic section, such as a hyperbola, a parabola, an ellipse and a circle. The shape does not need to be a full ellipse or a full circle. Because the shape may averagely follow the conic section, the shape may have a random or deterministic variation from an accurate shape.

The loop 410 may be made of a flexible material and/or it may comprise at least one joint (see example/embodiment related to FIG. 4A) for providing the flexibility to the loop 410 of potentially non-flexible material or for adding the flexibility to the loop 410 irrespective of the material. The first end 202 of the loop 410 of the elongated structure 200 is attached to the roof 106 of said cylindrical chamber 10, the first end 202 of the loop 410 belonging to the first portion 200. In an embodiment, the central axis CA may pass through the middle of the loop 410.

The loop 410 may comprise the at least one second portion 206, and each of the at least one second portion 206 has the second end 204. The at least one second end 204 of the elongated structure 114 is opposite to the first end 202 of the elongated structure 114. The at least one second portion 206 deviates from the central axis CA of the cylindrical chamber 10 within which it locates.

Figure 4C:
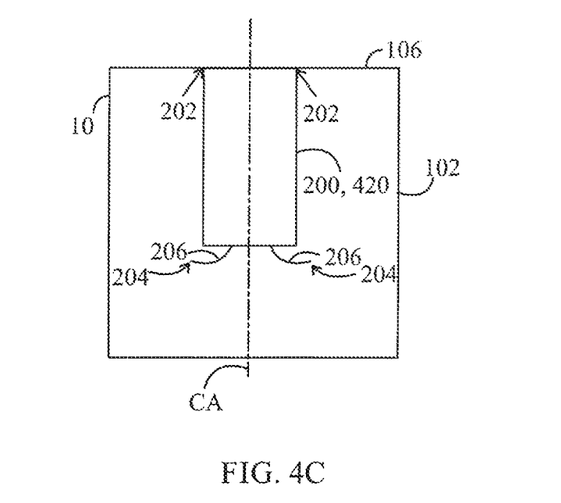

In an embodiment an example of which is illustrated in FIG. 4C, the elongated structure 114 may comprise an angular loop 420 as the first portion 200. The angular loop 420 may have a shape of a polygon, which may be regular or irregular. The angular loop 420 may comprise a triangle, a rectangle, a square or the like for example.

Figure 5:
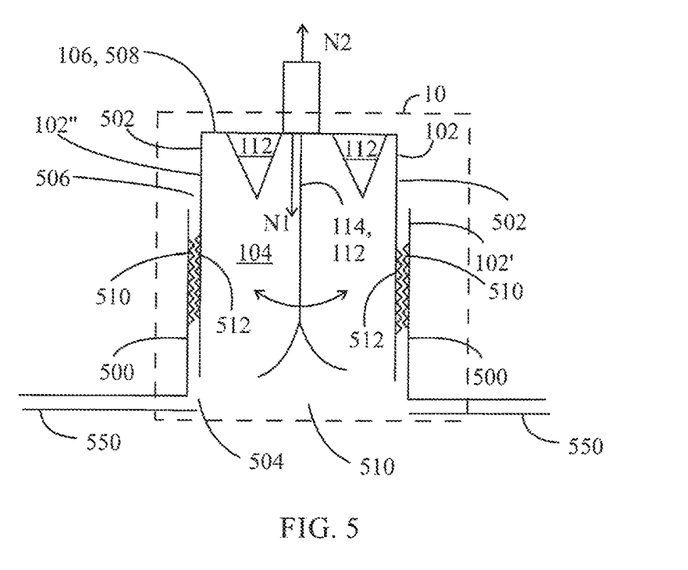
FIG. 5 illustrates an example of a cylindrical chamber comprising of two cylinders.

In an embodiment an example of which is illustrated in FIG. 5, at least one of the cylindrical chambers 10 may comprise a first cylinder 500, both ends 504, 506 of which are open. At least one of the cylindrical chambers 10 may comprise a second cylinder 502, one of ends 508 of the second cylinder 502 comprising the roof 106, and another of the ends 510 of the second cylinder 502 being open. The second cylinder 502 may reside within the first cylinder 500 such that the one of the ends 510, which is open, is deeper within the first cylinder 500 than the one of ends 508 comprising the roof 106. The wall 102 comprises a wall 102' of the first cylinder 500 and a wall 102" the second cylinder 502.

In an embodiment an example of which is illustrated in FIG. 5, the first cylinder 500 may comprise a thread 510 on an inner side of the wall 102' of the first cylinder 500. The second cylinder 502 may comprise a thread 512 on an outer side of the wall 102" of the second cylinder 502. The first cylinder 500 and the second cylinder 502 may be attached with each other with the threads 510, 512. The second cylinder 502 may move inward or outward a cavity 104 of the first cylinder 500 on a basis of a rotation of the thread 512 of the second cylinder 502 against the thread 510 of the first cylinder 500 while rotating the second cylinder 502 with respect to the first cylinder 500. When the second cylinder 502 is rotated such that it moves deeper in the first cylinder 500, the at least one electrode 112 that is fixed to the second cylinder 502 moves closer to the skin 304, which results in a more efficient electrical contact between the skin 304 and the at least one electrode 112.

The cylinders 500, 502 include the elongated structure 114, which may be or comprise a conductive spike on the roof 106. The elongated structure 114 may be a hook-like structure. The electrode apparatus 5 can be placed on a head or on other hairy body part of a mammal 20 and the elongated structure 114 is then twisted. The twisting force moves the hook-like elongated structure 114 inside the cylindrical chamber 10 and moves the hair out of the way of the electrodes 112. In an embodiment, this twisting force simultaneously may shorten the cylindrical chamber 10 and decrease the volume of the cylindrical chamber 10. This kind of deforming if the cylindrical chamber 10 may push conductive hydrogel, which may be within the cylindrical chamber 10, towards and in contact with the skin 304 disclosed from underneath the hair 300. Together with the elongated structure 114 and the conductive gel, the electrical pathway between the electrodes 112 and the skin 304 may be formed. An operator could simply twist each of the second cylinders 502 about five degrees every about fifteen minutes, for example, in order to administer more gel on the mammal's skin 304.

As shown in examples of FIGS. 1 and 5, a single cylindrical chamber 10 may comprise a first cylinder 500 and a second cylinder 502, which differ in diameter such that a second cylinder 502 fits inside a first cylinder 500. The first and second cylinders 500, 502 may comprise threads 510, 512 which may also be intertwining rails. Their rotation with respect to each other may decrease the overall length of a whole cylindrical chamber 10. The second cylinder 500 may therefore act like a screw top on the first cylinder 502.

In an embodiment, the elongated structure 114 may be immobile with respect to the roof 106, and the elongated structure 114 may rotate with the rotation of the first cylinder 500 with respect to the second cylinder 502.

Figure 6:
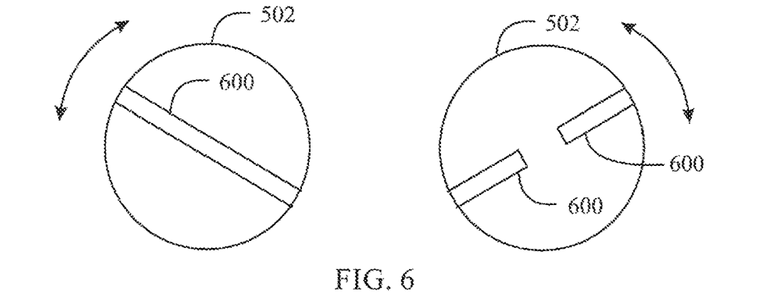
FIG. 6 illustrate examples of extension on cylindrical chambers.

In an embodiment an example of which is illustrated in FIG. 6, the roof 106 of the second cylinder 502 may comprise an extension 600. The extension 600 may be like a rectangular plate an edge of which is attached to the roof 106 on a side opposite to a side that is a part of the inner surface of the cavity 104 of the cylindrical chamber 10 (see also FIG. 5). A normal N2 of the edge of the extension 600 and a normal N1 of the side that is the part of the inner surface of the cavity 104 of the cylindrical chamber 10 are parallel. Directions of the normals N1 and N2 may be opposite. The extension 600 is a part that is designed to be operated with fingers, for example. By turning the extension 600, the second cylinder 502 may be rotated and moved inward in the cavity 104. By turning the extension 600 in the opposite direction, the second cylinder 502 may be rotated and moved outward in the cavity 104.

In an embodiment, the extension 600 is attached to the elongated structure 114, which is rotatable with respect to the roof 106, and the extension 600 is also rotatable with respect to the roof 106. Then the elongated structure 114 may be rotated round its longitudinal axis by rotating the extension 600 in order to bundle the hair 300. In general, the extension 600 may have a variety of shapes. The extension 600 may have a hole for a finger, for example. In an embodiment, the extension 600 may comprise two parts (see second cylinder on right in FIG. 6).

In an embodiment an example of which is illustrated in FIGS. 1 and 5, the electrode apparatus may comprise a support 550, which is attached on the skin 304 of the mammal 20. In an embodiment of FIGS. 7A and 7B, the support 550 may have a shape of a cap 700, which can be put on a head of the mammal 20 or a person. Here, the electrode cap comprises a combination of the cylindrical chambers 10 and the support 550. The cylindrical chambers 10 may be attached to the support 550 with a glue that is used for medical purposes. Signals from the electrodes 112 in the cylindrical chambers 10 may be fed to the data processing unit 50 for analyzing the signals.

Figure 8:
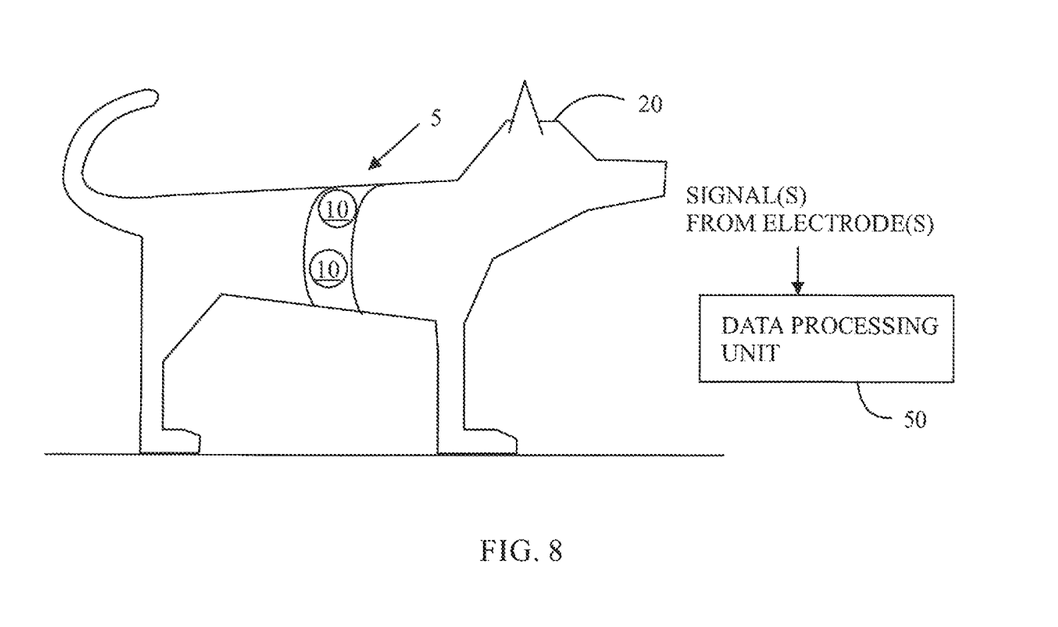
FIG. 8 illustrates an example of a band electrode arrangement.

In an embodiment an example of which is illustrated in FIG. 8, the support 550 may have a shape of band 800, which is put around a part of a body of the mammal 20. The mammal 20 may be a human being, a domestic animal, a wild animal or the like. Signals from the electrodes 112 in the cylindrical chambers 10 may be fed to the data processing unit 50 for analyzing the signals.

In an embodiment, a plurality of cylindrical chambers 10 may be attached to a base grid of the support 550 that may form a specific matrix. The matrix may be suitable for an EEG measurement to form 5/20-measurement setup on a mammal's head, without limiting to this. The support 550 may be made of PET-plastic (Polyethylene terephthalate plastic) material, for example, or some other polymer with a printed conductive layer that carries the measurement signal from the electrode(s) 112 of each individual cylindrical chamber 10. Together with the PET-layer, cup electrodes, skin adhesive layer and device connector it is possible to form easily applied single use disposable EEG electrode structure that may outperform the existing prior art measurement systems for the EEG. The support 550 may be disposable, and it could be offered in three or more different sizes to accommodate different user sizes.

In an embodiment, the cavity 104 is filled with an electrically conductive gel, which may be hydrogel. When the second cylinder 502 is rotated such that it moves deeper in the first cylinder 500, the at least one electrode 112 that is fixed to the second cylinder 502 moves closer to the skin 304. The movement of the second cylinder 502 deeper into the first cylinder 500 also causes pressure on the gel such that the gel is pushed towards and on the skin 304 in an efficient manner. The pressure of the electrically conductive gel against the skin 304 and movement of the at least one electrode 112 closer to or into a contact with the skin 304 results in a more efficient electrical contact between the skin 304 and the at least one electrode 112.

Figure 9:
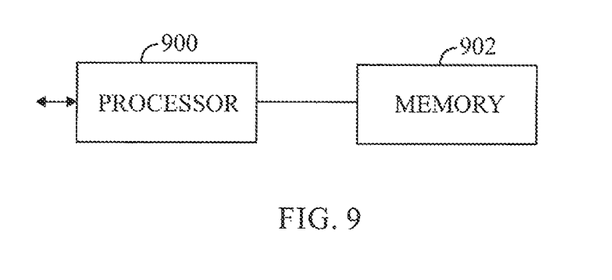
FIG. 9 illustrates an example of a data processing unit.

FIG. 9 illustrates an example of the data processing unit 50, which may comprise one or more processors 900 and one or more memories 902. The one or more memories may include a computer program code. The one or more memories 902 and the computer program code may be configured to, with the one or more processors 900, cause the data processing unit 50 at least to processes and analyse the signals from the electrodes 112.

Figure 10:
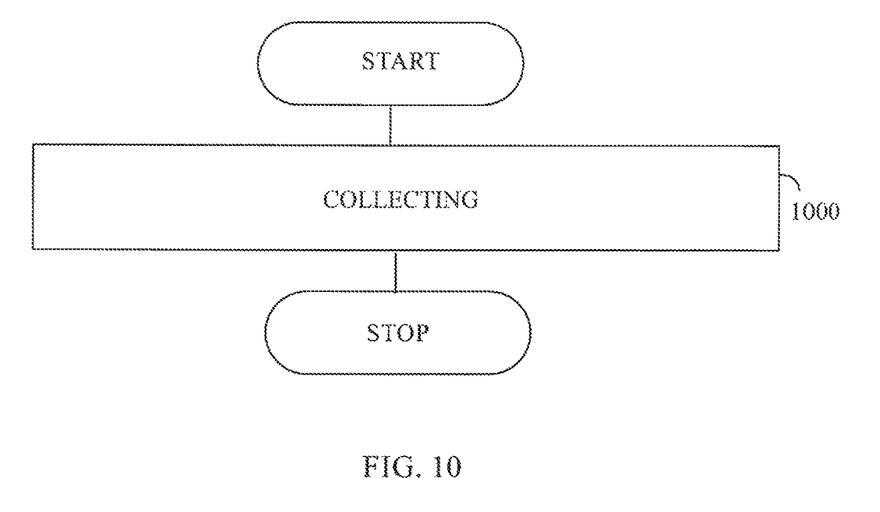
FIG. 10 illustrates of an example of a flow chart of a measuring method.

FIG. 10 illustrates a flow chart of the measurement method. In step 1000, hair 300 is collected in a bundle with an elongated structure 114, each of which is within a cylindrical chamber 10 of the electrode apparatus 5, in response to rotation of the elongated structure 114 for improving a contact of the at least one electrode 112, which is within the cylindrical chamber 10, with the skin 300 of the mammal 20.

As already explained, the electrode apparatus 5 comprises one or more cylindrical chambers 10. Each of the elongated structure 114 comprises a first portion 200 parallel to a central axis CA of a cylindrical chamber 10 within which the elongated structure 114 is. A first end 202 of the elongated structure 114 is attached to a roof 106 at a first end 108 of a cylindrical chamber 10 within which the elongated structure 114 is. The first end 202 of the elongated structure 114 belongs to the first portion 200. At least one second portion 206 of the elongated structure 114, each of the at least one second portion 206 comprising a second end 204 opposite to the first end 202 of the elongated structure 114, deviates from a direction of the central axis CA of a the cylindrical chamber 10 within which the elongated structure 114 is. Each cylindrical chamber 10 of the one or more cylindrical chambers 10 comprise a wall 102, which forms a cavity 104 within said cylindrical chamber 10. A second end 110 of said one or more of the cylindrical chambers 10 opposite to the first end 108 is open.

The EEG or ECG measurement can be performed without removing patient's hair and avoiding long set-up time. Another aspect is that a long training and experience needed for placing individual EEG electrodes on the head may be avoided. The electrodes can be positioned simply, which offers a fast way to measure extensive EEG data, for example. This, in turn, may yield cost and time savings on a critical EEG measurements. All in all, the proposed electrode apparatus may allow a much easier, faster and more reliable way of measuring EEG or ECG signal.

The solution described above provides advantages. No need to remove hair manually before the measurement. The electrode apparatus 5 provides a good or superior measurement comfort for both the operator and the mammal 20 that is measured. The electrode apparatus 5 may be made to be an easily applied single-piece electrode. The electrode apparatus 5 allows a prolonged measurement because of comfort and because of an added conductive gel with the pressure as a result of the twisting/rotation. The measurement is easy to start (no need to place separate single electrodes and cables). The measurement is reliable measurement, and a signal quality is good. The electrode apparatus can be mass-produced, and its manufacturing cost is relatively cheap solution, which allows a possibility for high revenue market. The electrode apparatus 5 is also MRI (magnetic resonance imaging) compliant because no magnetic materials are needed.

The method shown in FIG. 10 may be implemented as a logic circuit solution or computer program. The computer program may be placed on a computer program distribution means for the distribution thereof. The computer program distribution means is readable by a data processing device, and it encodes the computer program commands, carries out the measurements and optionally controls the processes on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

The invention claimed is:

1. An electrode apparatus configured to be applied on a skin with hair of a mammal for measuring an electrical bio-signal, wherein the electrode apparatus comprises:
    first and second cylindrical chambers,
    the first cylindrical chamber comprising a wall, which is configured to form a cavity within the first cylindrical chamber, and having both ends open,
    the second cylindrical chamber comprising a roof at a first end of the second cylindrical chamber, a second end of the second cylindrical chamber opposite to the first end being open, the roof covering a combination of the first and second cylindrical chambers, and
    at least one electrode; and
    an elongated structure, within both of the first and second cylindrical chambers, comprising a first portion parallel to a central axis of the first and second cylindrical chambers, a first end of the elongated structure, the first end of the elongated structure belonging to the first portion, being attached to the roof, and at least one second portion, each comprising a second end opposite to the first end, the at least one second portion being configured to deviate from a direction of the central axis of said first and second cylindrical chambers; and
    wherein the elongated structure is configured to rotate in order to bundle hair, the bundle of the hair being formed on and around the second portion of the elongated structure for exposing skin without the hair within both of the first and second cylindrical chambers, when applied to the mammal so as to improve a contact of the at least one electrode with the skin of the mammal.

2. The electrode apparatus of claim 1, wherein the elongated structure is rotatable with respect to the roof.

3. The electrode apparatus of claim 1, wherein the elongated structure is flexible.

4. The electrode apparatus of claim 1, wherein the elongated structure comprises polymer.

5. The electrode apparatus of claim 1, wherein the elongated structure comprises at least one bendable joint, which is configured to deviate the at least one second portion from the central axis.

6. The electrode apparatus of claim 1, wherein the elongated structure comprises the at least one electrode.

7. The electrode apparatus of claim 1, wherein the elongated structure comprises a shank as the first portion, and one or more bends, each of the bends being one of said at least one second portion.

8. The electrode apparatus of claim 1, wherein the elongated structure has a shape of at least one of the following: a hook, a letter L.

9. The electrode apparatus of claim 8, wherein the elongated structure is immobile with respect to the roof, and the elongated structure is configured to rotate with the rotation of the second cylindrical chamber.

10. The electrode apparatus of claim 8, wherein the electrode apparatus comprises a support, which is configured be attached on the skin of the mammal.

11. The electrode apparatus of claim 1, wherein:
the second cylindrical chamber is configured to reside within the first cylindrical chamber such that the open end of the second cylindrical chamber is deeper within the first cylindrical chamber than the one of the ends comprising the roof; and
wherein the wall comprises a wall of the first cylindrical chamber and a wall of the second cylindrical chamber.

12. The electrode apparatus of claim 11, wherein the first cylindrical chamber comprises a thread on an inner side of the wall of the first cylindrical chamber;
wherein the second cylindrical chamber comprises a thread on an outer side of the wall of the second cylindrical chamber; and
wherein the first cylindrical chamber and the second cylindrical chamber are configured to attach with each other with the threads, and the second cylindrical chamber is configured to proceed inward or outward a cavity of the first cylindrical chamber on a basis of a rotation of the second cylindrical chamber with respect to the first cylindrical chamber.

13. A measurement method of an electrode apparatus, wherein the electrode apparatus is applied on a skin with hair of a mammal for measuring an electrical bio-signal, the electrode apparatus comprising first and second cylindrical chambers, the method comprising:
collecting hair in a bundle with an elongated structure, which is within both of the first and second cylindrical chambers of the electrode apparatus, in response to rotation of the elongated structure for improving a contact of at least one electrode, with the skin of the mammal;
wherein the first cylindrical chamber comprises a wall, which is configured to form a cavity within the first cylindrical chamber, and having both ends open;
wherein the second cylindrical chamber comprises a roof at a first end of the second cylindrical chamber, a second end of the second cylindrical chamber opposite to the first end being open, the roof covering a combination of the first and second cylindrical chambers;
wherein the elongated structure comprises a first portion parallel to a central axis of the first and second cylindrical chambers, a first end of the elongated structure being attached to the roof, the first end of the elongated structure belonging to the first portion, and the elongated structure comprising at least one second portion, each comprising a second end opposite to the first end of the elongated structure, the at least one second portion of the elongated structure deviating from a direction of the central axis of the first and second cylindrical chambers within which the elongated structure is located;
wherein as a result of the collecting, the bundle of the hair is formed on and around the second portion of the elongated structure for exposing skin without the hair.

14. The method of claim 13, wherein the elongated structure is rotatable with respect to the roof.

15. The method of claim 13, wherein the elongated structure comprises at least one bendable joint, which is configured to deviate the at least one second portion from the central axis.

16. The method of claim 13, wherein the elongated structure comprises the at least one electrode.

17. The method of claim 13, wherein the elongated structure comprises a shank as the first portion, and one or more bends, each of the bends being one of said at least one second portion.

18. The method of claim 13, wherein:
wherein the second cylindrical chamber is configured to reside within the first cylindrical chamber such that the open end of the second cylindrical chamber is deeper within the first cylindrical chamber than the one of the ends comprising the roof; and
wherein the wall comprises a wall of the first cylindrical chamber and a wall of the second cylindrical chamber.

19. The method of claim 13, wherein the first cylindrical chamber comprises a thread on an inner side of the wall of the first cylindrical chamber;
wherein the second cylindrical chamber comprises a thread on an outer side of the wall of the second cylindrical chamber; and
wherein the first cylindrical chamber and the second cylindrical chamber are configured to attach with each other with the threads, and the second cylindrical chamber is configured to proceed inward or outward a cavity of the first cylindrical chamber on a basis of a rotation of the second cylindrical chamber with respect to the first cylindrical chamber.

20. The method of claim 13, wherein the elongated structure is immobile with respect to the roof, and the elongated structure is configured to rotate with the rotation of the second cylindrical chamber.

* * * * *